United States Patent
Rosinskaya et al.

(10) Patent No.: US 7,597,903 B2
(45) Date of Patent: Oct. 6, 2009

(54) METHOD AND COMPOSITION FOR PRODUCING CATHETERS WITH ANTIBACTERIAL PROPERTY

(75) Inventors: Cecilia Rosinskaya, Tel Aviv (IL); Amotz Weinberg, Tel Aviv (IL)

(73) Assignee: Shenkar College of Engineering and Design, Ramat Gan (IL)

( * ) Notice: Subject to any disclaimer, the term of this patent is extended or adjusted under 35 U.S.C. 154(b) by 443 days.

(21) Appl. No.: 10/307,501

(22) Filed: Dec. 2, 2002

(65) Prior Publication Data

US 2004/0106912 A1 Jun. 3, 2004

(51) Int. Cl.
*A61F 2/00* (2006.01)

(52) U.S. Cl. ..................... 424/426; 424/423

(58) Field of Classification Search ............ 424/1; 514/1

See application file for complete search history.

(56) References Cited

U.S. PATENT DOCUMENTS

| | | | | |
|---|---|---|---|---|
| 3,497,378 | A * | 2/1970 | Johnson et al. | 427/338 |
| 4,515,593 | A | 5/1985 | Norton | |
| 4,539,234 | A | 9/1985 | Sakamoto et al. | |
| 4,592,920 | A | 6/1986 | Murtfeldt | |
| 4,605,564 | A * | 8/1986 | Kulla et al. | 427/2.3 |
| 4,612,337 | A | 9/1986 | Fox, Jr. et al. | |
| 4,675,347 | A * | 6/1987 | Mochizuki et al. | 523/122 |
| 5,019,096 | A * | 5/1991 | Fox et al. | 600/36 |
| 5,089,205 | A | 2/1992 | Huang et al. | |
| 5,525,348 | A * | 6/1996 | Whitbourne et al. | 424/423 |
| 5,599,321 | A | 2/1997 | Conway et al. | |
| 5,804,318 | A * | 9/1998 | Pinchuk et al. | 428/421 |
| 5,830,883 | A * | 11/1998 | Block et al. | 514/55 |
| 5,945,457 | A * | 8/1999 | Plate et al. | 514/772.1 |
| 6,039,967 | A * | 3/2000 | Ottoboni et al. | 424/426 |
| 6,042,877 | A * | 3/2000 | Lyon et al. | 427/2.31 |
| 6,228,393 | B1 | 5/2001 | DiCosmo et al. | |
| 6,624,138 | B1 * | 9/2003 | Sung et al. | 514/1 |
| 6,797,743 | B2 * | 9/2004 | McDonald et al. | 523/122 |
| 2002/0034550 | A1 * | 3/2002 | Quong | 424/489 |
| 2002/0037874 | A1 * | 3/2002 | Renier et al. | 514/54 |
| 2002/0103526 | A1 * | 8/2002 | Steinke | 623/1.11 |
| 2002/0173775 | A1 * | 11/2002 | Modak et al. | 606/1 |

OTHER PUBLICATIONS

Ratner et al., Biomaterials Science: An Introduction to Materials in Medicine, 1996, Academic Press, p. 119.*
"Antimicrobial". Stedman's Medical Dictionary 27th Edition. Online. INternet. Accessed Feb. 14, 2006. <http://www.thomsonhc.com>.*
"Antibacterial". Stedman's Medical Dictionary 27th Edition. Online. INternet. Accessed Feb. 14, 2006. <http://www.thomsonhc.com>.*
"Microbe". Stedman's Medical Dictionary 27th Edition. Online. INternet. Accessed Feb. 14, 2006. <http://www.thomsonhc.com>.*
Bach A. Clinical Studies on the Use of Antibiotic and Antiseptic Bonded Catheters to Prevent Catheter-related Infection, Zentralblatt für Bakteriologie, 1995. 283(2). pp. 208-214.
Kohnen W et al , "Polymer Materials for the Prevention of Catheter-related Infections". Zentralblatt für Bakteriologie. 1995, 283(2). pp. 175-186.
Boswald M. et al , Antimicrobial Activity and Biocompatibility of Polyurethane and Silicone Catheters containing Low Concentrations of Silver: A New Perspective in Prevention of Polymer-associated Foreign-body-infections, Zentralblatt für Bakteriologie, 1995, 283(2), pp. 187-200.
Rosch W et al , "Catheter-Associated Infections in Urology: Possible Use of Silver-Impregnated Erlanger Silver Catheter", Infection, 1999. 27 Suppl 1. S74-77.
Raad I et al., "Silver Iontophoretic Catheter: A Prototype of a Long-term Anti-infective Vascular Access Device", The Journal of Infectious Diseases, Feb. 1996. 173(2). pp. 495-498.
Schierholz JM et al . "Investigation of a Rifampin, Fusidic-acid and Mupirocin Releasing Silicone Catheter", Biomaterials, 1998. 19. pp. 2065-2074.
Kamal GD. et al , "Reduced Intravascular Catheter Infection by Antibiotic Bonding". J A M A , 265, May 8, 1991, N 18, pp. 2364-2368.

(Continued)

*Primary Examiner*—M P Woodward
*Assistant Examiner*—Jennifer A Berrios
(74) *Attorney, Agent, or Firm*—Pearl Cohen Zedek Latzer, LLP

(57) ABSTRACT

A medical device and a method for imparting antibacterial properties to the device, made from hydrophobic polymer, particularly to urinary latex catheters comprises treatment of the device by spreading, dipping or spraying and consequent drying with natural biodegradable polymers (A), composition including a cross-linking agent (B) for partial cross-linking the mentioned polymer and an anti-microbial agent compatible with A and B. The polymer may be from a group of polysachharides, for example polyglucosamine-chitosan. For partial cross-linking of the polymer substances having aldehyde groups such as glucose or evolving aldehydes such as hexamethylenetetramine or their mixtures are used. The polymer is able to form on the surface of the medical device a thin film that swells in wet or moisturized state once inserted into the body. In the swollen state it will gradually release an anti-microbial agent.

12 Claims, No Drawings

OTHER PUBLICATIONS

Hashimoto H et al, "Basic Study on Antibacterial Urethral Catheter I, Development of a New Anti-bacterial Coating Material for Silicone Catheters", Kansenshogaku Zasshi. May 2000. 74(5), pp. 431-440.

Hashimoto H. et al, "Basic Study on Anti-bacterial Urethral Catheter II, Potency of a New Anti-bacterial Catheter and its Durability in Experimental Models", Kansenshogaku Zasshi. May 2000, 74(5), pp. 441-449.

Cho YH et al., "Prophylactic Efficacy of a New Gentamicin-releasing Urethral Catheter in Short-term Catheterized Rabbits". British Journal of Urology International, Jan. 2001. 87 (1). pp. 104-109.

Pugach JL et al, Antibiotic Hydrogel Coated Foley Catheters for Prevention of Urinary Tract Infection in a Rabbit Model, Journal of Urology, Sep. 1999. 162 (3 Pt 1), pp. 883-887.

Johnson JR et al, "Activities of a Nitrofurazone-containing Urinary Catheter and a Silver Hydrogel Catheter against Multidrug-resistant Bacteria Characteristic of Catheter-associated Urinary Tract Infection", Antimicrobial Agents and Chemotherapy, Dec. 1999, 43 (12), pp. 2990-2995.

Bach A et al. "Prevention of Bacterial Colonization of Intravenous Catheters by Antiseptic Impregnation of Polyurethane Polymers". Journal of Antimicrobial Chemotherapy, May 1994. 33(5). pp. 969-978.

Maki DG et al. "Study of a Novel Antiseptic Coated Central Venous Catheter". Critical Care Medicine, 1991, 19 (4) Suppl, S99.

Raad I et al, "The Broad-spectrum Activity and Efficacy of Catheters Coated with Minocycline and Rifampin", The Journal of Infectious Diseases, 1996, 173, pp. 418-424.

Liedberg H. et al, "Silver Alloy Coated Catheters Reduce Catheter-associated Bacteriuria". British Journal of Urology. 1990. 65. pp. 379-381.

Johnson JR et al, "Prevention of Catheter-associated Urinary Tract Infection with a Silver Oxide-coated Urinary Catheter: Clinical and Microbiologic Correlates", Journal of Infectious Diseases, 1990, 162. pp. 1145-1150.

Saint S et al, "Preventing Catheter-related Bacteriuria: Should we? Can we? How?", Archives of Internal Medicine, Apr. 26, 1999. 159. pp. 800-808.

Liedl B . "Catheter-associated Urinary Tract Infections". Current Opinion in Urology 2001, Jan. 11 (1). pp. 75-79.

Ahearn DG et al., "Effects of Hydrogel/silver Coatings on In Vitro Adhesion to Catheters of Bacteria Associated with Urinary Tract Infections". Current Microbiology. Aug. 2000, 41(2). pp. 120-125.

Godfrey H et al , "Catheterization and Urinary Tract Infections Microbiology". British Journal of Nursing, Jun. 8-21, 2000, 9(11), pp. 682-684, 686, 688-690.

Morris NS. et al , "The Development of Bacterial Biofilms on Indwelling Urethral Catheters". World Journal of Urology. Dec. 1999, 17 (6), pp. 345-350.

Kumamoto Y et al , "Comparative Studies on Activities of Antimicrobial Agents against Causative Organisms Isolated from Patients with Urinary Tract Infections" (1998) II Background of Patients. Japan Antibiotics, Apr. 2000. 43 (4), pp. 234-248.

Tyagi M et al . "Preparation and Anti-bacterial Evaluation of Urinary Balloon Catheter". Biomedical Science Instrumentation. 1997. 33. pp. 240-245.

Sedor J et al, "Hospital-acquired Urinary Tract Infections Associated with the Indwelling Catheter". Urological Clinique of North America. Nov. 1999. 26 (4), pp. 821-828.

Simhi E. et al, "Effect of the Adhesive Antibiotic TA on Adhesion and Initial Growth of E coli on Silicon Rubber". FEMS Microbiol Lett, Nov. 2000. 1:192(1): pp. 97-100.

Riley DK et al , "A Large Randomized Clinical Trial of a Silver-impregnated Urinary Catheter: Lack of Efficacy and Staphylococcal Superinfection", Am J Med. Apr. 1995. 98(4): pp. 349-356.

* cited by examiner

METHOD AND COMPOSITION FOR PRODUCING CATHETERS WITH ANTIBACTERIAL PROPERTY

BACKGROUND OF THE INVENTION

This invention relates to the prevention of infections associated with medical devices disposed long-term in a body.

More particularly, the invention provides a coating containing anti-bacterial agents for slow release into the environmental space with which the device is in contact. It is to be applied on healthcare devices such as urinary latex or other polymeric catheters, urethral stents for residence within a portion of the body through which aqueous biological fluids pass.

A medical device with anti-bacterial property is intended to prevent the spreading and penetration of the bacteria from the place of the entrance of the medical device into the body of the patient and consequent infection. The purpose of this invention is to create a method and composition for the treatment of the outer and/or the inner surface of the medical device for rendering it anti-microbial property without any change in the performance and properties of the device.

Catheter-associated urinary tract infection is the most common nosocomial infection and is a major problem with severe consequences, that cause prolongation of hospitalization time and contribute to patient suffering. This problem becomes especially critical for patients using a long-term indwelling urinary catheter. The latter, if it remains in the body for a prolonged time, is the basis for initial adherence of microorganisms to the device's polymeric surface with consequent growth of bacteria on the catheter surface and production of bio-film.

Anti-microbial therapy alone, generally, is not sufficient to cure the patient of these infections, and frequent replacement of the catheter remains the only method for possible treatment of the sick person.

Development of catheters with anti-adhesive and/or anti-infective properties is a plausible approach to the prevention of such infections. Anti-adhesive polymeric catheters may prevent adherence of microorganisms to the medical device surface; anti-infective polymers contain anti-microbial substances which are incorporated into the polymer's matrix or bound to the polymer's surface and act as a drug release system that leads to reduction or prevention of infection.

The problem of producing urinary catheters with anti-infective property and slow release ability is very complicated. There are many patents and research papers that offer different versions of solutions to the mentioned problem.

The anti-bacterial properties may be imparted to the catheter by two methods.

The first is using the polymers with anti-bacterial properties that are delivered by insertion of an anti-bacterial agent or medicine into the polymer matrix through process of production of medical device. This method has severe restrictions—the structure of the polymer matrix is very dense and hinders the migration of the anti-bacterial agent from inner space to outer surface of device and as a result—negligible anti-bacterial effect is achieved. In addition anti-bacterial agents and/or medicines should be compatible with the substances used for producing the polymer and all the ingredients must be stable at the time of production. The production usually requires high temperatures and pressure.

The second method of rendering anti-bacterial properties to the medical devices consists of the treatment of the medical device with anti-microbial agent by one of following ways—dipping, spraying, spreading and linking the former to the polymer surface of the medical device. However, almost all the medical devices are made from synthetic polymers such as polyethylene, polypropylene, polytetrafluoroethylene, polyvinylchloride, polymethylmethacrilate, polyurethane or latex (natural or synthetic rubber) and have a smooth, hydrophobic surface without any active chemical groups able to interact with an antibacterial agent. Thus after treatment some quantity of the anti-bacterial agent remains on the surface of device but it cannot be linked and does not provide a drug-release effect.

Detailed discussion of catheter related infections and the means of prevention was a topic at the 1st National Workshop on Catheter Infections in Cologne (Germany) in 1994.

Prior art ways of rendering the anti-microbial ability to polymeric medical devices are described in the following patents and articles.

U.S. Pat. No. 5,019,096 offers a method of preparing an infection-resistant medical device comprising one or more matrix-forming polymers selected from the group, consisting of biomedical polyurethane, silicones and biodegradable polymers and anti-microbial agent especially a synergistic combination of a silver salt and chlorhexidine (or its salts) wherein the matrix is effective to provide controlled release of anti-microbial agent within a portion of the human body.

U.S. Pat. No. 5,599,321 claims a sustained release bactericidal cannula or catheter for residence within a portion of a human body, that has a polymer matrix and an anti-bacterial agent residing within. The polymer matrix includes cured silicone rubber and within the antibacterial agent—finely divided nitrofuran compound which can effectively prevent proliferation of certain bacteria. The anti-microbial agent can diffuse out of the polymeric matrix into an aqueous biological environment when the polymeric matrix comes into contact with it.

U.S. Pat. No. 5,089,205 claims the process for imparting enhanced anti-microbial properties to medical devices that involves dipping the device into a latex composition and prior to curing or heating dipping the already coated forms into a second composition containing an anti-bacterial agent and thereafter curing the finally produced device such as gloves, before stripping from a forming apparatus.

One of the widely developed methods of enhancement of the anti-bacterial properties of medical devices (catheters) from synthetic polymers is based on the usage of metals and especially silver which possesses anti-bactericidal potency.

A Division of Bard Medical introduced the Bardex J.C. Catheter that is produced by sputtering micro-particles of silver to form a thin layer on the surface. Bardex J.C. Catheter material yields negligible zones of inhibition for bacteria but no catheter-associated urinary tract infections occurred during the first three months.

Böswald M. et al determined the antibacterial activity of polyurethane and silicone catheters, containing low concentration of silver, that was introduced by precipitation of silver chloride in the polymer matrix. The method of attaching of bactericidal property comprises swelling of the catheter in methanol, ethanol, isopropanol or acetone and immersing with compounds containing silver in ethanolamine.

U.S. Pat. No. 4,592,920 describes method for the production of anti-microbial catheter with an anti-microbial metal compound powder having particle size to about 30μ in diameter. The comminuted antimicrobial metal compound is suspended in a suspending agent which can be cured to form a catheter or which can be formed to provide a coating on a previously formed catheter.

Impregnation of urological catheter with silver oxide has given inconsistent results. Riley and Johnson found no significant reduction in the rate of bacteriruria, when catheters with silver oxide were evaluated in a large number of patients.

Liedelberg found that silver alloy catheters were significantly more effective in preventing bacteriuria than silver oxide catheters.

The level of anti-microbial activity of silver depends on the chemical structure and the technique used for binding the silver to the catheter matrix. Taking into account very low solubility of silver and its derivatives, the efficacy of this treatment would not be significant.

Many inventors and researchers have tried to find a method of surface treatment of catheters.

U.S. Pat. No. 4,612,337 describes the method of preparing infection-resistant polymeric materials for use outside or within human body which comprises the following sequence of steps: soaking a polymeric material with a solution of an anti-microbial agent such as sodium sulfadiazine, oxacilline, dissolved in an organic solvent, thereafter soaking the polymeric material in an organic solvent such as ethanol for a metal salt such as silver nitrate, resoaking the polymeric material with the solution of antimicrobial agent dissolved in the organic solvent thereafter. The polymeric material is dried after each step, finally the treated catheter has on the surface a coating of antimicrobial agent—silver sulphadiazine.

Cook Critical Care manufactures catheters (polyethylene) that are treated with antibiotic-cefazoline which is bonded to the surface of the catheter by the cationic surfactant—tridodecylmethylammonium chloride (TDMAC).

Cook Critical Care also produces the central venous catheters impregnated with a combination of two antibiotics: minocycline and rifampin, that are bonded to the surface of the catheter through TDMAC. Both antibiotics have broad spectrum activity against various nosocomial pathogens.

The ionic linking of TDMAC to hydrophobic uncharged surface of polyethylene is doubtful due to the absence of any active groups in polyethylene.

Pugach developed an antibiotic liposome (ciprofloxacin liposome) containing hydrogel for external coating of silicone Foley catheter. The treated catheter shows 30% decrease in cases of bacteriuria compared to untreated catheters.

Hashimoto et al developed antibacterial and antiadherent coating for silicone catheters on the base of the mixture of soybean lecithin as anti-adherent component, silver citrate as anti-bacterial agent and liquid silicone. The treated urinary catheter has anti-microbial activity to Gram-positive and Gram-negative bacteria.

Simhi E. treated the silicone rubber catheter with TA adhesive antibiotic that decreases adhesion and initial growth of *Esherichia coli*.

U.S. Pat. No. 4,539,234 describes a process for producing an urethral catheter capable of preventing urinary tract infections, which comprises of forming a film having functional groups capable of being converted into ion-exchange groups by hydrolysis on the inside and/or outside wall of urethral catheter composed of olefin polymer, diene or silicone polymer. The ion-exchange groups are carboxyl groups that are obtained by reacting a copolymer of maleic acid anhydride and a copolymerizable compound with a polyfunctional compound having hydroxyl groups under a condition of an excess amount of the copolymer and thereafter hydrolyzing the acid anhydride groups.

Johnson J. R. et al compared the anti-microbial activity of a nitrofurazone-coated urinary catheter (NFC) and a silver hydrogel urinary catheter (SHC) and found that in-vitro NFC is markedly superior that the SHC in some respects.

Maki et al studied a novel triple-lumen polyurethane central venous catheter coated with silver sulfadiazine and chlorhexidine and found that antiseptic coated catheters were two-fold less likely to be colonized than untreated and four-fold less likely to produce bacteremia.

All the catheters with coating, impregnated with an anti-bacterial agent and containing an anti-bacterial agent within polymer matrix, develop their anti-bacterial action gradually—at first by contact with environmental wet medium there is a high initial release rate, the so-called "burst effect", depending on a number of parameters: mass, distribution and solubility of the anti-bacterial agent within the polymer or on its surface, strength of adhesion, degree of swelling of the film on the surface of the medical device, properties of the components of the used composition. Usually the rate of release of an antibacterial agent at the initial period is relatively high. The second continuous period is controlled by the structure of the polymeric matrix, if the antibacterial agent is within it, or by the degree of swelling of the coating on the surface.

A large part of the "burst effect" could be removed simply by cleaning the catheter surface.

The described methods of enhancement of the anti-bacterial property of the medical device, in particular catheters, are not likely to give a complete solution to the problem due to a multiplicity of factors defining the processes of adhesion and release of anti-bacterial agent, for example the compatibility of anti-bacterial agent and the synthetic polymeric device, and their other properties.

It is therefore one of the objects of the present invention to obviate the disadvantages of prior coatings and to provide a catheter with a coating that releases an anti-bacterial agent in a predictable manner.

It is a further object of the present invention to provide a method for the manufacture of the coated catheter.

DESCRIPTION OF THE INVENTION

There are no diagrams. Two tables of test results appear hereinafter.

The present invention achieves the above objects by providing a medical device coated at least on its outer surface with a slow-release antibacterial composition, said composition comprising a mixture of:
 a biodegradable polymer swelling when in contact with body fluids;
 a cross-linking agent causing partial cross-linking of said polymer; and
 an anti-microbial agent compatible with said polymer and said cross-linking agent and slowly releasable therefrom on swelling of said polymer.

In a preferred embodiment of the present invention there is provided a medical device wherein said polymer is a polysaccharide.

In a most preferred embodiment of the present invention there is provided method for coating a medical device, comprising the steps:
a) preparing an aqueous solution of a biodegradable polymer, a cross-linking agent causing partial cross-linking of said polymer, and an anti-microbial agent compatible with said polymer and said cross-linking agent;
b) applying said solution to said device; and
c) drying the medical device Many further embodiments of the invention will be described hereinafter. The method and composition for rendering of anti-microbial property to a medical device made of synthetic polymer consists of the creation of a thin film on the surface of the medical device from substances able to adhere to the hydrophobic surface of the polymeric device. The film swells in the wet or moisturized state whilst simultaneously releasing an anti-bacterial agent or medicine. The proposed composition includes a polymeric substance (A) that forms a thin film, and a substance (B) for full or partial cross-linking of the afore-mentioned polymeric compound and an antibacterial agent (C), compatible with A and B.

All the compounds of the composition: A, B, C are biocompatible with human tissue and are not allergenic, cytotoxic, thrombogenic and have no additional side effects.

This invention relates to medical devices for use in the body, including all the types of catheters such as central venous, urinary and other health-care devices, made from latex (synthetic or natural rubber) with or without surface silicone coating.

Long-term indwelling urinary catheters are the principal cause of recurring urinary tract infections that cause patient suffering.

It is known that usually catheter-related infections are introduced into the body through the place of the insertion of the catheter. The intra-luminal space of the urinary catheter is continuously rinsed by flowing urine and is small. The presence of foreign substances in the intra-luminal space may cause a urine flow stoppage.

This leads to the conclusion that only the outer surface of the urinary catheter needs to be treated. Thus, the present invention is concerned with a composition for the treatment of the outer surface of the latex urinary Foley catheter.

According to fore-mentioned problems it is reasonable to choose as substance A one of the natural biodegradable polymers: alginates, derivatives of cellulose or chitin etc., that can potentially be fully or partially cross-linked with formation of net structure which will swell in the wet state. The antimicrobial agent or medicine is stored in the cells of the net structure and is released during swelling.

The following natural polymer is used: chitosan-deacetylated chitin, polyglucosamine, cationic polymer, biodegradable, nontoxic, non-allergenic, with anti-bacterial and fungistatic properties, compatible with antibacterial agents and medicines of cationic character, with molecular weight $10^4$-$10^6$ and degree of deacetylation 75 to 87%.

Chitosan and its derivatives are widely used for medical and healthcare aims: wound dressing, biocompatible implants, surgical sewing threads thanks to its ability to promote wound healing.

Chitosan is water-soluble and to decrease its solubility it is possible to arrange partial cross-linking with substances that have aldehyde groups or evolve same substances with aldehyde groups that are capable of forming a net structure. The latter is able to swell in a wet or moisturized state, to hold any substance in the cells of the net and to release it during swelling. The cross-linking of chitosan in-situ, on the surface of the medical device, assists in its adhesion to this surface.

The degree of cross-linking of the polymer defines the basic properties of the film: the degree of swelling, smoothness, brittleness, elasticity, power of adhesion and the rate of release of the antibacterial agent embedded in the polymeric net structure.

The chitosan's film adheres to the inert and hydrophobic surface of the catheter by non-polar intermolecular forces, that keep it on the surface in the wet state through swelling.

Substances containing aldehyde groups or evolving aldehydes, interact with amino groups of chitosan, decreasing water solubility. These agents are for example dextrose, hexamethylenetetramine or their mixtures. The reaction between chitosan and cross-linking agents occurs at a range of temperatures 65-95° C.

Anti-bacterial agents or medicines should have cationic or nonionic character for compatibility with chitosan and broad spectrum of anti-bacterial activity, for instance chlorhexidine, quaternary ammonium compounds, urotropin and other substances without charge. The quantity of the anti-bacterial agent is dependent on its minimal inhibition concentration (MIC) for any type of bacteria and is sufficient for preventing the adherence of pathogenic microorganisms to the catheter, following multiplication of bacteria and formation of biofilm.

The compositions described in the present invention may be stored without change to its properties and appearance for a long period of time because the anti-bacterial agent does not interact with chitosan and is kept in the polymer's net only by slight inter-molecular forces.

After treatment a thin film with a weight of 0.4-1.0 mg/cm$^2$ is formed on the surface of the device. This film is able to swell in the wet or moisturized state at the ratio of 3-10 (ratio of weight of wet and dry film) and to release the antibacterial agent into the environmental space with which it is in contact.

The treated medical device, such as a catheter, after insertion into the body shows a bacteriostatic effect because of the swelling of the natural polymer on its surface and the release of said anti-bacterial agent or medicine.

The medical device is made from a synthetic polymer, has hydrophobic, inert and smooth outer and internal surfaces and after treatment the appearance and physico-mechanical properties of the device remain unchanged The appearance of the treated urinary catheter is satisfactory. The surface is smooth and there is no hindrance to catheter insertion.

The treatment of the catheters or any medical device may be achieved by spreading (spraying) equally the mentioned composition on the whole or any part of the outer surface or by dipping the whole or any part of the device in the composition and subsequent drying. The treated devices show the anti-bacterial effect determined as "zone of inhibition" of growth of bacteria for any period of time.

The present invention provides a medical device, such as a urinary latex Foley catheter, with effective anti-microbial properties, having the ability to release an anti-microbial agent or medicine during its presence in the body. Enhancement of anti-microbial property of the surface of the catheter is achieved by treatment of any part, that will be inserted into the body, with the composition, comprising as a base 1-4% (w/w) viscous solution of the natural polymer-polyglucosamine-chitosan, 0.5-5.0% of own weight of chitosan (dry) cross-linking agent and anti-bacterial agents or medicines. The catheter may be treated by dipping, spraying or spreading and drying with hot air.

Chitosan dissolves in a 1-1.5% solution of acetic acid at room temperature, solutions are viscous, colorless and transparent, and can be stored without any change for a long time. The viscosity of the chitosan solution is regulated by its concentration and is stipulated by the technical method of the treatment of catheter: dipping, spraying or spreading.

The viscous composition through the treatment fills in all the irregularities on the surface of the catheter and owing to the contact between surface and composition the produced film adheres to the surface through the drying.

For the cross-linking of chitosan substances containing aldehyde groups or evolving aldehydes capable of interacting with amino groups of chitosan are used. For instance, dextrose, hexamethylenetetramine, their mixtures etc. The sequence of this interaction is the formation of a net structure that is able to swell and release the anti-bacterial agent into the environment in the body.

Through cross-linking in-situ the polymer with the net structure adheres to the surface of the catheter and remains on it in the form of a thin film.

The quality of this coating is dependent on the properties and quantities of chitosan, the cross-linking and anti-bacterial agents in the composition. The concentration of the cross-linking agent is an important parameter and reflects on the physico-mechanical properties of the film, degree of swelling, the ability to hold and to release the anti-bacterial agents and medicines.

It is preferable to choose an anti-bacterial agent among the substances with cationic character because they are compatible with chitosan and do not change the structure of the composition. For this purpose an anti-bacterial agent from the group biguanides may be used, for example chlorhexidine digluconate (diacetate), from the group of quaternary ammonium compounds (benzalkonium chloride etc), silver compounds for example silver sulphadiazine, etc.

All the components of the composition are compatible, have no allergenic, thrombogenic or any negative side effects on human tissue.

The composition may be stored for a long time at room temperature without any changes to its properties.

Quality of the anti-bacterial treatment of the urinary catheter is assessed by the following parameters: bacteriostatic effect (Z.I.), long term stability, appearance of the treated catheter.

Bacteriostatic and/or fungistatic effect is determined as value of zone inhibition (Z.I.) of bacteria development on the inoculated layer of agar-agar.

The width of zone inhibition is measured as the whole width zone on both sides of the catheter. For assessment of significance of the measured value Z.I. it should be compared with the value of Z.I. for an untreated catheter. According to experience it is plausible to determine the efficiency of the anti-bacterial treatment as ratio (n) of area of Z.I. for treated and untreated catheter.

$$n = \frac{Si}{So},$$

So—area (mm$^2$) of Z.I. of untreated catheter
Si=area (mm$^2$) of Z.I. of treated catheter The value of 'n' takes into account that, according to the results of trials, the anti-bacterial agent is released from the catheter and penetrates into the agar-agar along the axis of the catheter and across it.

In this way it is plausible to compare the results of the determination of the bacteriostatic effect for various experimental or practical cases.

For assessment of long-term stability of the anti-bacterial effect trials over different periods of time are required. The appearance of the treated catheter: it must be smooth and should not cause difficulties when inserted into the body.

The anti-bacterial agents or medicines that are used for this target may have bacteriostatic or/and fungistatic effect to different types of bacteria: Gram-positive (*Staphilococcus aureus*), Gram-negative (*Esherichia coli*), yeasts, fungi, and correspondingly the treated catheter acquires these properties.

The described examples will make apparent to those skilled in the art how further forms of the invention may be realized.

EXAMPLES

A. Preparation of the Solution of Chitosan

Example 1

4.0 g chitosan (high molecular weight—$10^5$-$10^6$) with degree of deacetylation 75-85% is mixed at room temperature by stirring with 96 ml of 1.5% (w/w) solution of acetic acid until full dissolution is achieved. The solution is homogenous, transparent, and may be stored for a long time.

B. Preparation of Composition

Example 2

The composition for anti-bacterial treatment of the urinary Foley latex catheter contains 4% w/w solution of chitosan 2.5% of weight of chitosan (dry) dextrose, 5 g/kg chlorhexidine digluconate. Preparation of said composition includes addition to 100 g of 4% (w/w) solution of chitosan from example 1, 1 ml of 10% (w/w) solution of dextrose, mixing, then the addition of 2.5 ml of 20% solution of chlorhexidine digluconate and stirring.

Example 3

The composition for anti-bacterial treatment of the urinary Foley latex catheter contains 4.2 (w/w) solution of chitosan, 1.0% of own weight of chitosan (dry) dextrose, 7 g/kg chlorhexidine digluconate. Preparation of said composition includes addition to 100 g of 4.2% solution of chitosan, prepared as said in Example 1, of 4.2 ml of 10% solution of dextrose, careful mixing up of the solution, addition 3.5 ml of 20% solution of chlorhexidine digluconate, careful mixing at room temperature.

Example 4

The composition for anti-bacterial treatment of the urinary Foley latex catheter contains 3.6% (w/w) solution of chitosan, 2.0% of own weight of chitosan (dry) dextrose, 3.0 g/kg of composition of chlorhexidine diacetate. Preparation of the composition includes addition to 100 g of 3.6% solution of chitosan, prepared as in Example 1, 0.72 ml of 10% solution of dextrose, careful mixing up, addition 3 ml of 10% solution of chlorhexidine diacetate and mixing up.

Example 5

The composition for the anti-bacterial treatment of the urinary Foley latex catheter contains 3.0% (w/w) solution of chitosan, 3.0% of own weight of chitosan (dry) hexamethylenetetramine (HMTA), 3.0 g/kg chlorhexidine digluconate. Preparation of the composition includes addition to 100 g of 3.0% solution of chitosan, prepared as in Example 1, 0.9 ml 10% (w/w) solution of HMTA, mixing up, addition of 1.5 ml of 20% solution of chlorhexidine digluconate and careful mixing up.

Example 6

The composition for the anti-bacterial treatment of the urinary Foley latex catheter contains 3.8% (w/w) solution of chitosan, 5.0% of own weight of chitosan (dry) HMTA. Preparation of the composition includes addition to 100 g of 3.8% solution of chitosan, prepared as in Example 1, 1.9 ml of 10% solution of HMTA and careful mixing up.

Example 7

The composition for the anti-bacterial treatment of the urinary Foley latex catheter contains 3.8% (w/w) solution of chitosan, 8% of own weight of chitosan (dry) HMTA. Preparation of the composition includes addition to 100 g of 3.8% solution of chitosan, prepared as in Example, 1.3 ml of 10% solution of HMTA and mixing up.

Example 8

The composition for the anti-bacterial treatment of the urinary Foley latex catheter contains 4.2% solution of chitosan, 1% of own weight of chitosan (dry) HMTA, 3.0 g/kg chlorhexidine digluconate. Preparation of the composition includes: addition to 100 g of 4.2% solution of chitosan, prepared as in Example 1, 0.42 ml 10% solution of HMTA, careful mixing up, addition 1.5 ml of 20% solution of chlorhexidine digluconate and mixing up.

Example 9

The composition for the anti-bacterial treatment of the urinary Foley latex catheter contains 3.7% solution of chitosan, 2% of own weight of chitosan (dry) HMTA and 7.0 g/kg chlorhexidine digluconate. The preparation of the composition includes addition to 100 g of 3.7% w/w solution of chitosan, prepared as in Example 1, 0.74 ml of 10% solution HMTA, careful mixing up, addition 3.5 ml of 20% solution chlorhexidine digluconate and mixing up.

Example 10

The composition for the anti-bacterial treatment of the urinary Foley latex catheter contains 4.0% w/w solution of chitosan, 1% of own weight of chitosan (dry) dextrose, 1% of own weight of chitosan (dry) HMTA, 5.0 g/kg chlorhexidine digluconate. The preparation of the composition includes addition to 100 g of 4.0% w/w solution of chitosan, prepared as in Example 1, 0.4 ml of 10% solution dextrose, mixing up, addition 0.4 ml of 10% solution HMTA, mixing up, addition 2.5 ml of 20% solution of chlorhexidine digluconate and mixing up.

Example 11

The composition for the anti-bacterial treatment of the urinary Foley latex catheter contains 4.1% w/w solution of chitosan, 2.0% of own weight of chitosan (dry) dextrose, 1.0% of own weight of chitosan (dry) HMTA, 7.0 g/kg chlorhexidine digluconate. The preparation of the composition includes addition to 100 g of 4.1% solution of chitosan, prepared as in the Example 1, 0.82 ml of 10% solution dextrose, careful mixing up, addition of 0.41 ml 10% solution or HMTA, careful mixing up, addition 3.5 ml 20% solution of chlorhexidine digluconate and mixing up.

Example 12

The composition for the anti-bacterial treatment of the urinary Foley latex catheter contains 3.7% w/w solution of chitosan, 1.5% of own weight of chitosan (dry) dextrose, 5% of own weight of chitosan (dry) HMTA. The preparation of the composition includes adding to 100 g of 3.7% viscous solution of chitosan, prepared as in Example 1, 0.5 ml of 10% solution of dextrose, carefull mixing up, addition of 1.85 ml of 10% solution HMTA and mixing.

Example 13

The composition for the anti-bacterial treatment of the urinary Foley latex catheter contains 2.5% w/w solution of chitosan, 1.0% of own weight of chitosan (dry) dextrose, 3.0% of own weight of chitosan (dry) HMTA, 3.0 g/kg of weight of composition of dichlorhexidine digluconate. The preparation of composition includes addition to 100 g of 2.5% solution of chitosan, prepared as in Example 1, 0.25 ml of 10% solution of dextrose, careful mixing up, 0.63 ml of 10% solution of HMTA, mixing up, addition of 1.5 ml 20% solution chlorhexidine digluconate and mixing up.

Example 14

The composition for the anti-bacterial treatment contains 2.5% w/w solution of chitosan, 1% of own weight of chitosan (dry) HMTA, 4.0 g/kg of composition chlorhexidine digluconate. The preparation of the composition includes addition to 100 g 2.5% solution of chitosan, prepared as in Example 1, 0.25 ml of 10% solution HMTA, careful mixing up, addition of 2 ml of 20% solution of chlorhexidine digluconate and mixing up.

Example 15

The composition for the anti-bacterial treatment of the urinary Foley latex catheter contains 2.2% solution of chitosan, 1.0% of own weight of chitosan (dry) dextrose, 3.0 g/kg of composition chlorhexidine digluconate. The preparation of the composition includes addition to 100 g of 2.2% solution of chitosan, prepared as in Example 1, 0.22 ml of 10% solution dextrose, mixing up, addition 1.5 ml of 20% solution chlorhexidine digluconate and careful mixing up.

Example 16

The composition for the anti-bacterial treatment of the urinary Foley latex catheter contains 2.2% solution of chitosan and 5.0% of own weight of chitosan HMTA. The preparation of the composition includes addition to 100 g of 2.2% solution of the chitosan, prepared as in Example 1, 1.1 ml of 10% solution HMTA and careful mixing up.

Example 17

The composition for the anti-bacterial treatment of the urinary Foley latex catheter contains 3.6% (w/w) solution of chitosan, 1% of own weight of chitosan (dry) of dextrose, 1.0 g/kg of chlorhexidine digluconate. The preparation of the composition includes addition to 100 g of 3.6% solution of chitosan, prepared as in Example 1, 0.36 ml of 10% solution of dextrose, mixing up, addition of 0.5 ml of chlorhexidine digluconate and mixing.

C. Treatment of the Medical Devices (Urinary Foley Latex Catheter).

Example 18

The portion of the outer surface of urinary silicone treated Foley latex catheter (natural rubber) is uniformly treated by spreading with the composition prepared according to procedures, described within examples 2-12, 17. The treated part of the catheter is dried by hot air at at the temperature 90-95° C. The treated part of the catheter is smooth and does not hinder insertion of the catheter into the body.

Example 19

The portion of the urinary Foley latex catheter to be treated is dipped into the composition described in the examples 13-16 for 15-30 seconds and dried by hot air at the temperature 90-95° C. After drying there is a very thin and smooth film on the outer surface of the catheter that swells in a wet state and doesn't hinder insertion of the catheter into the defined part of the body.

D. Testing of Anti-bacterial Properties of the Treated Catheters.

Example 20

The anti-microbial activity of treated in previous examples 2-17 catheters was assessed by a modified Rizly-Bauer technique. Septicemia strains of two microorganisms: *Staphylococcus aureus* and *Escherichia coli* were independently grown according to procedure described in (Jssam Raad, Rabih Darouche 1996). A twenty millimeters sample of catheter was put and pressed into the agar-agar overlaid with microorganisms and incubated at 37° through the defined intervals of time. Zone inhibition of the growth of the microorganisms along the axis and there-across was assessed by measuring the distance in mm perpendicular and along the axis of the tested piece of the catheter. Besides the measuring of the zone inhibition was recorded absence or presence of microorganisms under the sample.

There was no growth of microorganisms under all the evaluated samples of catheter.

The results of the assessment of the anti-bacterial activity of the treated samples of catheters as values of width and length of zone inhibition and ratio of the area of zone inhibition for treated and untreated samples are represented in table 1.

Consequently all the values of width and length of Z.I. and ratio of areas, that are shown in table 1, confirm the high efficiency of the treatment with described composition.

In addition the long term effect of anti-bacterial action of the treated catheter was assessed after 1, 3 and 7 days. The results are shown in the table 2. The data of the table point out on the long-time action of the anti-bacterially treated catheters.

TABLE 1

Antibacterial Efficiency (Z.I.) of Treated Examples of Catheter

| Example no. | *Staphylococcus aureus* width mm | length mm | n | *Escherichia coli* width mm | length mm | n |
|---|---|---|---|---|---|---|
| untreated | 1 | 20 | — | 1 | 20 | — |
| 2 | 10 | 25 | 13 | 11 | 24 | 13 |
| 3 | 11 | 26 | 14 | 10 | 25 | 13 |
| 4 | 10 | 23 | 12 | 10 | 24 | 12 |
| 5 | 16 | 27 | 22 | 15 | 25 | 19 |
| 6 | 17 | 26 | 22 | 16 | 27 | 22 |
| 7 | 19 | 27 | 26 | 20 | 27 | 27 |
| 8 | 9 | 23 | 10 | 9 | 24 | 11 |
| 9 | 12 | 25 | 15 | 11 | 25 | 14 |
| 10 | 9 | 24 | 11 | 10 | 24 | 12 |
| 11 | 10 | 26 | 13 | 12 | 25 | 15 |
| 12 | 11 | 24 | 13 | 13 | 25 | 16 |
| 13 | 8 | 22 | 9 | 9 | 24 | 11 |
| 14 | 9 | 23 | 10 | 9 | 24 | 11 |
| 15 | 8 | 21 | 8 | 10 | 22 | 11 |
| 16 | 11 | 23 | 13 | 11 | 24 | 13 |
| 17 | 8 | 22 | 9 | 7 | 23 | 8 |

TABLE 2

The Values of Width (mm) of The Zone Inhibition Of The Treated Samples of Catheter

| No. of examples | *Staphylococcus aureus* | | | *Escherichia coli* | | |
|---|---|---|---|---|---|---|
| | 1 Day | 3 Days | 7 Days | 1 Day | 3 Days | 7 Days |
| 2 | 10 | 11 | 10 | 11 | 10 | 9 |
| 3 | 11 | 10 | 11 | 10 | 8 | 10 |
| 5 | 16 | 14 | 13 | 15 | 14 | 13 |
| 6 | 17 | 14 | 12 | 16 | 12 | 11 |
| 7 | 19 | 15 | 11 | 20 | 15 | 12 |
| 9 | 12 | 11 | 12 | 11 | 12 | 10 |
| 11 | 10 | 9 | 10 | 12 | 11 | 10 |
| 12 | 11 | 10 | 11 | 13 | 11 | 12 |
| 13 | 8 | 7 | 8 | 9 | 8 | 10 |
| 14 | 9 | 8 | 9 | 9 | 10 | 8 |
| 15 | 8 | 8 | 8 | 10 | 9 | 9 |
| 16 | 11 | 9 | 7 | 11 | 10 | 10 |
| 17 | 8 | 7 | 8 | 7 | 8 | 6 |

The scope of the described invention is intended to include all embodiments coming within the meaning of the following claims. The foregoing examples illustrate useful forms of the invention, but are not to be considered as limiting its scope, as those skilled in the art will readily be aware that additional variants and modifications of the invention can be formulated without departing from the meaning of the following claims.

We claim:

1. A medical device coated with a slow-release antibacterial composition, the slow-release antibacterial composition comprising a mixture of chitosan and dextrose, thereby forming a polymeric network wherein the concentration of said dextrose is between 0.5 and 5.0% of dry chitosan; and
   a cationic antibacterial agent which is chlorhexidine or benzalkonium chloride, compatible with said chitosan and said dextrose, wherein said cationic antibacterial agent is embedded in said polymeric net-work;
   wherein said slow-release antibacterial composition swells upon being contacted with body fluids and releases said cationic antibacterial agent.

2. The medical device as claimed in claim 1, wherein said medical device is a urinary catheter.

3. The medical device as claimed in claim 1, wherein said chitosan has a molecular weight at the range of $10^4$ to $10^6$ and a degree of deacetylation at the range of 75% to 87%.

4. The medical device of claim 1, wherein the said chitosan is used at concentration in a solution in the range of between 1.5 to 4.5 (w/w) %.

5. The medical device as claimed in claim 1, wherein said chlorhexidine is in the form of chlorhexidine diacetate and/or chlorhexidine digluconate.

6. The medical device of claim 5, wherein said chlorhexidine is in the form of chlorhexidine digluconate or chlorhexidine diacetate and is present at a range of concentrations of between 2.0 to 10.0 g/kg of slow-release antibacterial composition.

7. A method for coating a medical device according to claim 1 comprising the steps:
preparing an aqueous solution of a biodegradable chitosan, wherein the chitosan is dissolved in water solution of acetic acid at concentrations between 1.0 to 1.5%;
adding dextrose, and chiorhexidine or benzalkonium chloride, compatible with said chitosan and said dextrose;
applying said aqueous solution to said medical device; and
drying said medical device.

8. The medical device as claimed in claim 1, wherein said dextrose is used at range of concentrations between 0.5 to 2.0% of weight of dry chitosan.

9. The medical device as claimed in claim 1, wherein said cationic antibacterial agent is benzalkonium choride.

10. The medical device as claimed in claim 9, wherein the concentration of said benzalkonium choride is at a range of concentrations between 5.0 to 20.0 g/kg of the slow-release antibacterial composition.

11. The medical device of claim 6, wherein the said chlorhexidine diacetate is used at range of concentrations between 3.0 to 6.0 g/kg of the slow-release antibacterial composition.

12. The medical device of claim 6, wherein the chlorhexidine digluconate is used at range of concentrations between 3.0 to 6.0 g/kg of the slow-release antibacterial composition.

\* \* \* \* \*